US007088828B1

(12) United States Patent
Bradford et al.

(10) Patent No.: US 7,088,828 B1
(45) Date of Patent: Aug. 8, 2006

(54) METHODS AND APPARATUS FOR PROVIDING PRIVACY FOR A USER OF AN AUDIO ELECTRONIC DEVICE

(75) Inventors: Richard W. Bradford, Westford, MA (US); Philip Jacobs, Windham, NH (US)

(73) Assignee: Cisco Technology, Inc., San Jose, CA (US)

( * ) Notice: Subject to any disclaimer, the term of this patent is extended or adjusted under 35 U.S.C. 154(b) by 0 days.

(21) Appl. No.: 09/548,539

(22) Filed: Apr. 13, 2000

(51) Int. Cl.
*H03B 29/00* (2006.01)
*A61F 11/06* (2006.01)
*G10K 11/16* (2006.01)
*H04R 3/02* (2006.01)

(52) U.S. Cl. .................... 381/71.1; 381/73.1; 704/226; 379/406.02

(58) Field of Classification Search ............... 381/71.1, 381/71.2, 71.4, 71.7–71.9, 71.11–71.13, 73.1; 379/406.01, 406.06, 406.02; 704/226
See application file for complete search history.

(56) References Cited

U.S. PATENT DOCUMENTS 2,043,416 A * 6/1936 Lueg ......................... 381/71.1
3,879,578 A * 4/1975 Wildi ........................ 381/73.1
4,122,303 A * 10/1978 Chaplin et al. ............ 381/71.8
4,417,098 A * 11/1983 Chaplin et al. .......... 381/71.12
4,473,906 A * 9/1984 Warnaka et al. ........... 381/73.1
4,654,871 A * 3/1987 Chaplin et al. ............... 381/72
5,105,377 A * 4/1992 Ziegler, Jr. .................. 708/300
5,377,276 A * 12/1994 Terai et al. .............. 381/71.11
5,526,421 A * 6/1996 Berger et al. .......... 379/406.06
5,559,893 A 9/1996 Krokstad et al. ............. 381/71
5,627,746 A * 5/1997 Ziegler et al. ................ 700/55
5,675,658 A 10/1997 Brittain ....................... 381/72

(Continued)

OTHER PUBLICATIONS

Kuo, Sen M., et al. "Adaptive Multi-Channel On-Line Modeling Algorithm for 3-D Active Noise Control Systems", 1992, IEEE Industrial Electronics Society, 18th Anual Conference, pp. 1331-1335.*

(Continued)

*Primary Examiner*—Xu Mei
(74) *Attorney, Agent, or Firm*—BainwoodHuang

(57) ABSTRACT

The invention is directed to techniques for suppressing the voice of a user of an audio electronic device, such as a mobile phone, from being heard by an unintended listener. In one arrangement, the invention includes an input microphone, an electronics module, and a suppression speaker. The user speaks into the input microphone, and the electronics module generates an antivoice signal from a voice signal received from the input microphone. The suppression speaker outputs an antivoice output that combines with the voice of the user to form a voice suppression zone next to the speaker. The user thus can carry on his or her conversation in private as long as the unintended listener is within the voice suppression zone. Alternately, the user can avoid distracting other users of similar devices nearby, such as in a crowded office environment with many individuals using telephones at the same time. In another arrangement, the invention includes multiple suppression speakers that can be oriented in different directions to provide one or more voice suppression zones.

18 Claims, 10 Drawing Sheets

U.S. PATENT DOCUMENTS

| | | | | |
|---|---|---|---|---|
| 5,825,897 | A | 10/1998 | Andrea et al. | 381/71.6 |
| 5,848,168 | A | 12/1998 | Shipps et al. | 381/71.5 |
| 5,848,169 | A * | 12/1998 | Clark et al. | 381/71.13 |
| 5,937,070 | A | 8/1999 | Todter et al. | 381/71.6 |
| 6,108,415 | A | 8/2000 | Andrea | 379/433 |
| 6,112,103 | A | 8/2000 | Puthuff | 455/557 |
| 6,275,592 | B1 * | 8/2001 | Vartiainen | 381/71.11 |
| 6,690,800 | B1 * | 2/2004 | Resnick | 381/73.1 |
| 6,754,353 | B1 * | 6/2004 | Cheng | 381/71.1 |
| 6,952,474 | B1 * | 10/2005 | Wittke et al. | 379/406.02 |
| 2005/0065778 | A1 * | 3/2005 | Mastrianni et al. | 704/200.1 |

OTHER PUBLICATIONS

Yeh, Hen-Geul. "Adaptive Noise Cancellation for Speech with a TMS32020", 1987, International Conference on Acoustics, Speech, and Signal Processing, vol. 2, pp. 1171-1174.*

Billoud Guy, et al. "The Use of Time Algorithms for the Realization of an Active Sound Attenuator", May 23-26, 1989, International Conference on Acoustics, Speech, and Signal Processing, vol. 3, pp. 2025-2028.*

* cited by examiner

METHODS AND APPARATUS FOR PROVIDING PRIVACY FOR A USER OF AN AUDIO ELECTRONIC DEVICE

BACKGROUND OF THE INVENTION

Telephone technology provides users of the phone with a readily available means of communicating over long distances. A typical telephone or other audio communication device provides a microphone that the user speaks into, a communication link between the user and another party, and a speaker that provides the other party's voice to the user. Over time, audio communication technology has come to include mobile phones, such as cellular phones, satellite phones, and other devices.

Noise cancellation techniques exist to reduce unwanted noise that may interfere with audio communication, such as unwanted noise that interferes with a user listening to another party on a telephone or a headset device. Active noise reduction (ANR) techniques provide a sound wave that is out of phase with the unwanted noise. For example, in an airplane, an ANR technique provides an antinoise sound wave designed to mask or greatly reduce the noise of jet engines so that pilots or passengers in the airplane may use headsets in the airplane without distraction. The ANR technique includes using a microphone to detect a sound, such as the jet engine, electronic circuitry to produce an antinoise sound wave opposite in phase to the noise, and a speaker to broadcast the antinoise sound wave into or near a user's ear, such as through a headset that the user is wearing or from a location near the user's ear. The antinoise sound wave destructively interferes with the noise. The result is the reduction of the noise to a more comfortable level for the user.

SUMMARY OF THE INVENTION

At times, when talking on a mobile phone or other audio communication device, users desire to have a private conversation without strangers overhearing them. For example, an individual may use a cellular phone in a crowded airport, where finding a private room or space is difficult, if not impossible. The user of the cellular phone can turn to face a wall or corner of the room, but a stranger nearby may still overhear the conversation. The user may resort to various strategies, such as referring to topics in a cryptic or clipped manner or speaking in a very soft tone, but these approaches may interfere with the flow of the conversation with the party on the other end of the conversation. Such users desire to have a mobile phone that they can speak into privately and carry on conversations freely without being heard by unintended listeners that the user does not want to overhear the conversation. These same concerns apply to any number of audio electronic devices, such as two-way radios, personal tape recorders, laptop computers, and other devices used in the presence of such unintended listeners.

In other situations, users are distracted by conversations occurring near them, such as in a telemarketing office environment, where many workers carry on phone conversations in small cubicles adjacent to each other. Such workers desire to have a less distracting and noisy environment where they may concentrate on their own conversations. Such concerns apply to any environment where workers use telephones in cubicles, where enclosed offices are not available to most workers. In this situation, workers desire to suppress the noise of other conversations so that they may concentrate more effectively on their own work.

Thus, there is a need to eliminate or suppress unwanted voices overheard by unintended listeners, both from the standpoint of the users of an audio electronic device and unintended listeners seeking to avoid a distraction.

The invention thus provides a way to suppress the voice of the user of an audio electronic device. The invention provides a separate voice suppression speaker that projects an antivoice output directed outwardly away from the audio electronic device into a suppression zone where the antivoice output destructively interferes with the voice of the user. An unintended listener in the voice suppression zone hears a reduced voice that is difficult to hear clearly or understand. The audio electronic device can also include two or more voice suppression speakers which have different orientations from each other.

In one embodiment, an audio electronic device comprises an audio privacy feature for suppressing a voice, including an input microphone, an electronics module, and a suppression speaker. The input microphone generates a voice signal in response to a voice input. The electronics module receives the voice signal from the input microphone and generates an antivoice signal based on the voice signal. The suppression speaker receives the antivoice signal from the electronics module and generates an antivoice output from the antivoice signal. The antivoice output combines with the voice to form a voice suppression zone adjacent to the suppression speaker. In the voice suppression zone, the voice is attenuated so that it is difficult to understand by a listener located in the voice suppression zone.

The electronics module also includes, in another arrangement, an inverter and a delay module. The inverter inverts the voice signal into the antivoice signal so that the antivoice signal is opposite in phase to the voice signal. The delay module introduces a delay in the antivoice signal so that the antivoice output generated from the delayed antivoice signal is opposite in phase to the voice input.

In one arrangement, the delay introduced by the delay module is based on the distance from the input microphone to the suppression speaker. In another arrangement, the delay module controls the length of the signal based on a feedback signal. In alternate arrangements, the feedback signal is based on the antivoice signal or the antivoice output. If based on the antivoice output, the audio electronics device further includes a feedback microphone that receives the antivoice output.

Another arrangement of the audio electronics device includes a transmitter, a receiver, and a personal speaker for the user of the device to that the device can communicate with other devices. In other arrangements, the audio electronic device is a phone device, such as a wireless, hand-held phone, or a computerized device.

In one embodiment, an audio electronic device comprises an audio privacy feature for suppressing a voice, including an input microphone, an electronics module, and suppression speakers. The input microphone generates a voice signal in response to a voice input. The electronics module receives the voice signal from the input microphone and generates an antivoice signal based on the voice signal. The suppression speakers receive the antivoice signal from the electronics module and generate an antivoice outputs from the antivoice signal. The antivoice outputs combine with the voice to form one or more voice suppression zones adjacent to the suppression speakers. In each voice suppression zone, the voice is attenuated so that it is difficult to understand by a listener located in the voice suppression zone.

In one arrangement, the electronics module includes an inverter and a delay module. The inverter inverts the voice signal into the antivoice signal so that the antivoice signal is opposite in phase to the voice signal. The delay module introduces a delay in the antivoice signal so that the antivoice outputs generated from the delayed antivoice signal are opposite in phase to the voice input.

In one embodiment, an electronics module for use in a privacy device suppressing a voice includes a voice signal input, an antivoice signal output, and a controller. The controller receives the voice signal from the voice signal input and generates the antivoice signal based on the voice signal. The antivoice signal enables a suppression speaker to generate an antivoice output based on the antivoice signal that combines with the voice to form a suppression zone adjacent to the suppression speaker.

In one arrangement, the electronics module also includes a delay module. The controller inverts the voice signal into the antivoice signal so that the antivoice signal is opposite in phase to the voice signal. The delay module introduces a delay in the antivoice signal so that the antivoice output is opposite in phase to the voice input.

Another arrangement of the electronics module includes a feedback signal input receiving a feedback signal representative of the delayed antivoice signal.

In a further arrangement, the antivoice signal is a digital signal and the electronics modules includes a shift register and a digital-to-analog converter. The shift register introduces the delay into the digital antivoice signal. The digital-to-analog converter generates an analog antivoice signal from the delayed digital voice signal. In another arrangement, the antivoice signal is an analog signal, and the electronics module includes an analog-to digital-converter.

In another embodiment, the invention is a method for suppressing a voice received by an unintended listener to the voice. The method includes providing a voice signal based on the voice of a user, generating an antivoice signal based on the voice signal, and generating an antivoice output based on the antivoice signal that combines with the voice in order to suppress the voice received by the unintended listener located in a voice suppression zone formed by the antivoice output.

In one arrangement, the method includes inverting the voice signal to provide the antivoice signal so that the antivoice signal is opposite in phase to the voice signal, adding a delay to the antivoice signal, and generating the antivoice output based on the delayed antivoice signal.

The method also includes in another arrangement determining the delay based on the distance from the location of voice input to the location of the antivoice output. In one arrangement, this distance is the distance from the input microphone to the suppression speaker.

In another arrangement, the method includes controlling the length of the delay in the antivoice signal based on a feedback signal. In alternate arrangements, the feedback signal is based on the antivoice signal or the antivoice output.

In a further arrangement, the method includes orienting a direction of the antivoice output to direct the voice suppression zone to encompass a target location.

Another embodiment of the invention is directed to a computer program product that includes a computer readable medium having instructions stored thereon for suppressing a voice received by an unintended listener to the voice. The instructions cause a computer to receive a voice signal based on the voice of a user, generate an antivoice signal based on the voice signal, and output the antivoice signal so that the antivoice signal enables the generating of an antivoice output based on the antivoice signal that combines with the voice in order to suppress the voice received by the unintended listener located in a voice suppression zone formed by the antivoice output.

In one arrangement, the instructions cause the computer to invert the voice signal to provide the antivoice signal so that the antivoice signal is opposite in phase to the voice signal, add a delay to the antivoice signal, and generate the antivoice output based on the delayed antivoice signal.

A further embodiment of the invention is directed to a computer program propagated signal product that is embodied in a propagated medium having instructions stored thereon for suppressing a voice received by an unintended listener to the voice. For example, the propagated signal can be a radio signal carried by a radio wave, or an electrical signal propagated over the Internet or other network. The instructions cause a computer to receive a voice signal based on the voice of a user, generate an antivoice signal based on the voice signal, and output the antivoice signal so that the antivoice signal enables the generating of the antivoice output based on the antivoice signal that combines with the voice in order to suppress the voice received by the unintended listener located in a voice suppression zone formed by the antivoice output.

In one arrangement, the instructions cause the computer to invert the voice signal to provide the antivoice signal so that the antivoice signal is opposite in phase to the voice signal, add a delay to the antivoice signal, and generate the antivoice output based on the delayed antivoice signal.

The above-described features of the invention are well suited for use with devices manufactured by Cisco Systems, Inc. of San Jose, Calif.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

The invention is directed to techniques for suppressing the voice of a user of an audio electronic device, such as a mobile phone, to provide privacy for the user of the device and prevent an unintended listener from understanding the message delivered by the voice. The techniques involve generating an antivoice signal based on a voice signal representative of the voice of the user, and then outputting the antivoice signal as an antivoice output that suppresses the voice at the location of the unintended listener. The antivoice output and the voice combine to produce a combined sound that is difficult or impossible for the unintended listener to understand. The techniques include providing plural antivoice outputs oriented in different directions. The above-described features of the invention are well suited for use with devices manufactured by Cisco Systems, Inc. of San Jose, Calif.

Figure 1:
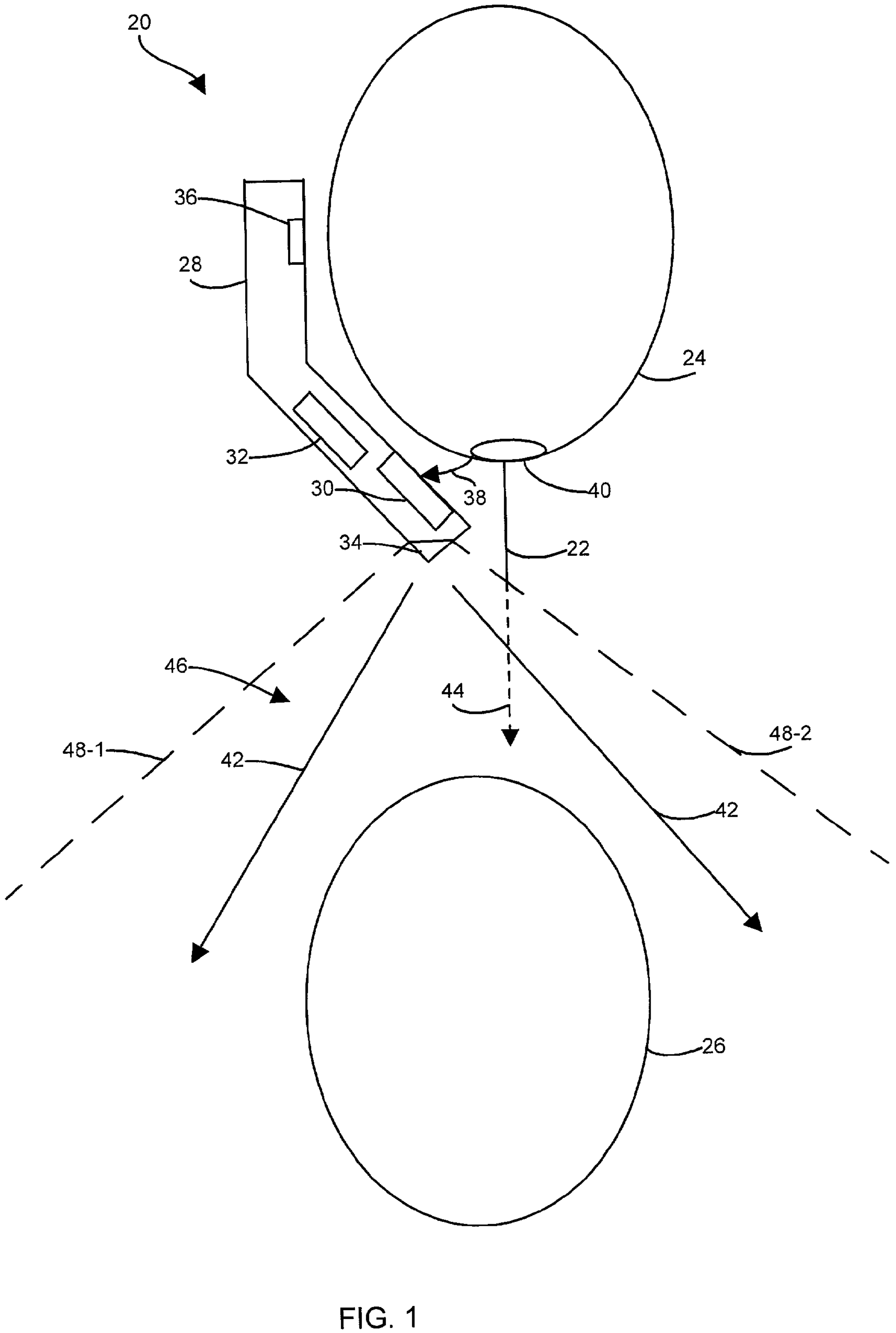
FIG. 1 shows, by way of example only, an overhead view of an audio privacy system including a mobile phone device having an input microphone, an electronics module, a personal speaker, and a suppression speaker generating a voice suppression zone encompassing an unintended listener.

FIG. 1 shows an audio privacy system 20 that is suitable for use by a user 24 speaking with his or her voice 22 into a mobile phone 28 that may be overheard by an unintended listener 26. The mobile phone 28 includes a input microphone 30 for receiving a voice input 38 from the mouth 40 of the user 24, an electronics module 32, a personal speaker 36 for the user 24, and a suppression speaker 34 that produces an antivoice output 42 that forms a voice suppression zone 46 adjacent to the suppression speaker 34.

In general, the mobile phone 28 is a moveable or portable mobile radio communication system, such as a cellular phone, cordless phone, or other types. In one arrangement, the mobile phone 28 is a wireless phone device, such as a cellular phone or wireless telephone device, capable of two-way radio communication with other devices, including mobiles phones 28, of the same type.

The voice suppression zone 46 is a three dimensional volume defined by the output of the suppression speaker 34 within which the antivoice output 42 from the suppression speaker 34 combines with the voice 22 to form a suppressed voice output 44. The voice 22 is suppressed by decreasing the volume of the voice 22, distorting the voice 22, or otherwise attenuating the voice 22 to produce a suppressed voice output 44 within the voice suppression zone 46. Typically, the unintended listener 26 is not able to distinguish the content of any message conveyed by the voice 22, as long as the unintended listener is located in the voice suppression zone 46.

The boundaries of the voice suppression zone 46 are shown in FIG. 1 by the zone boundaries 48-1 and 48-2, which are not meant to be limiting and are shown by way of example only. The zone boundaries 48-1 and 48-2 in FIG. 1 are lines representative of a three dimensional boundary zone beyond which the volume of the antivoice output 42 is at a sufficiently low level so that the antivoice output 42 does not combine effectively with the voice 22 to form the suppressed voice output 44. In other words, at a location just beyond the boundary 48-1 or 48-2 and outside of the voice suppression zone 46, the audio pattern of the voice 22 can be detected as opposed to detecting the audio pattern of the suppressed voice output 44, which is a combination pattern representing the combined voice 22 and antivoice output 42.

The design of the mobile phone 28 places the input microphone 30 closer to the user's mouth 40 than the suppression speaker 34. In a preferred arrangement, the input microphone 30 should be as close to the user's mouth 40 as possible. The design of the mobile phone 28 also provides a physical separation between the input microphone 30 and the suppression speaker 34 to give the electronics module 32 and the suppression speaker 34 enough time to generate an antivoice output 42. The mobile phone 28 also provides a limited physical barrier to the voice 22.

The user 24 can also move the voice suppression zone 46 by moving the mobile phone 28 (e.g. by redirecting a hand holding the phone) so as to direct the suppression speaker 34 in a particular direction to encompass an unintended listener 26 located in that direction. In one arrangement, the mobile phone 28 has a movable suppression speaker 34 that the user 24 moves in a particular direction to encompass an unintended listener 26.

Figure 2:
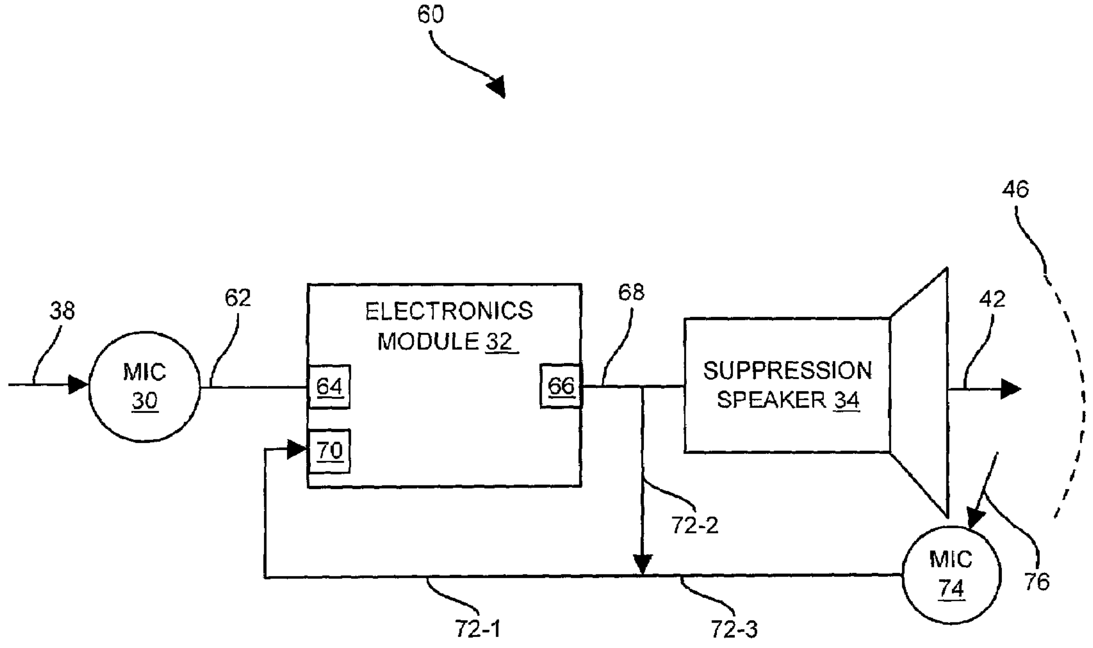
FIG. 2 shows a block diagram of an arrangement of an audio electronics device, including an input microphone, an electronics module, a suppression speaker, a feedback microphone, and a voice suppression zone.

FIG. 2 provides further details of the invention and illustrates an audio electronic device 60 suitable for use with the audio privacy system 20 of FIG. 1. The audio electronic device 60 includes the input microphone 30, the electronics module 32, the suppression speaker 34, and, optionally, a feedback microphone 74. The input microphone 30 receives the voice input 38 and outputs a voice signal 62 to a voice signal input 64 on the electronics module 32. The electronics module 32 outputs the antivoice signal 68 through the antivoice signal output 66 of the electronic module 32 to the suppression speaker 34. The suppression speaker 34 outputs the antivoice output 42 from the suppression speaker 34 to form a voice suppression zone 46 adjacent to the suppression speaker 34. The electronics module 32 receives a feedback signal 72-1 through the feedback signal input 70. In one arrangement of the invention, the feedback signal 72-1 is a feedback signal 72-2 based on the antivoice signal 68. In an alternate arrangement, the feedback signal 72-1 is a feedback signal 72-3 received from the feedback microphone 74, which receives a feedback input 76 based on the antivoice output 42.

The voice input 38 is a sound wave produced by the user 22, and the antivoice output 42 is a sound wave produced by the suppression speaker 34. The input microphone 30 and feedback microphone 74 are microphones suitable for use with an audio electronic device 60, such as microphones used with mobile phones as is known to those skilled in the art. The suppression speaker 34 is a speaker suitable for use with the audio electronic device, such as speakers used with mobile phones as is known to those skilled in the art.

In one arrangement, the voice signal 62, antivoice signal 68, and feedback signal 72 are implemented as digitized electronic signals. In another arrangement, the voice signal 62, antivoice signal 68, and feedback signal 72 are implemented as analog electronic signals. In a further arrangement, one or more of the voice signal 62, antivoice signal 68, and feedback signal 72 are implemented as a digital signal and one or more of them are implemented as an analog signal. Correspondingly, in one arrangement, the electronics module 32 and its components are implemented using analog circuitry. In another arrangement, the electronics module 32 and its components are implemented using digital circuitry. In a further arrangement, some components of the electronics module 32 are implemented using analog circuitry and some components are implemented using digital circuitry. Thus, for example, in one arrangement, the electronics module 32 receives an analog voice signal 62 and outputs a digital antivoice signal 68.

In another arrangement, the electronics module 32 is implemented on an integrated circuit (IC), such as an ASIC (application-specific integrated circuit) or other IC, installed on a printed-circuit board (PCB) and in communication with the input microphone 30, the feedback microphone 74, and the suppression speaker 34 through PCB connections. The use of an ASIC for the electronics module 32 is efficient in terms of cost and power consumption.

Figure 3:
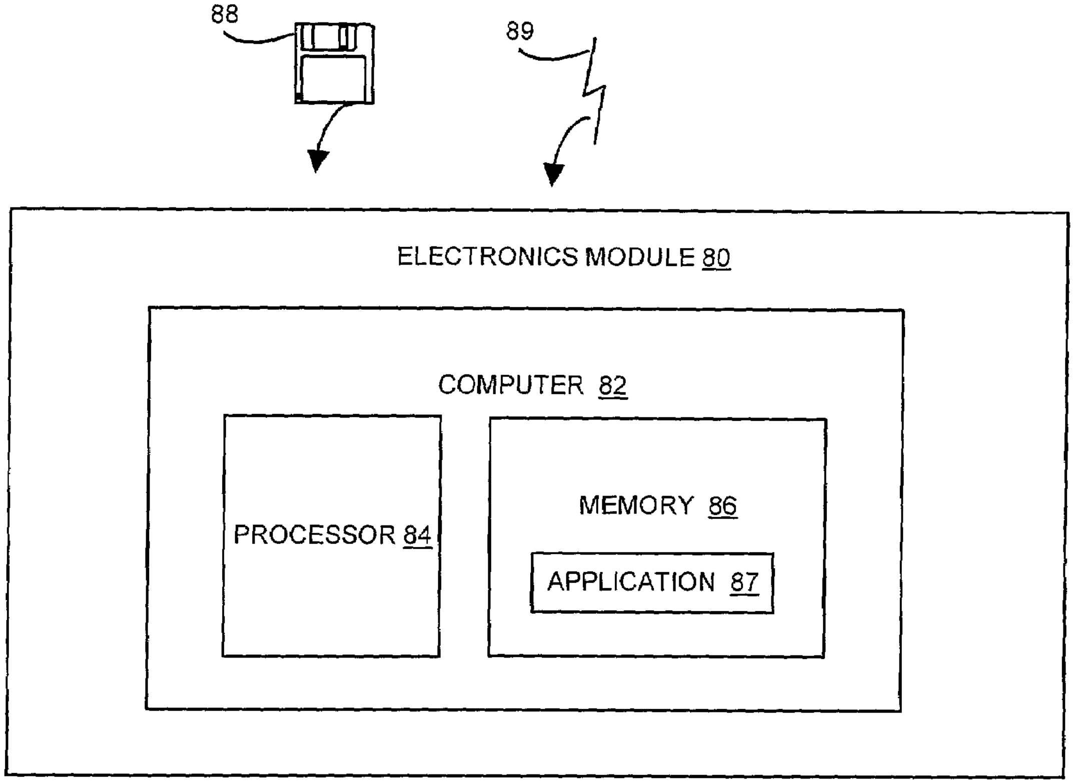
FIG. 3 provides, by way of example only, a block diagram of an electronics module suitable for use as one instance of the electronics module shown in FIG. 2, including a computer having a processor and memory.

The electronics module 32 is implemented as any suitable combination of software instructions and hardware circuitry. FIG. 3 provides, by way of example only, additional detail for an electronics module 80 suitable for use in one arrangement of the electronics module 32 shown in FIG. 2. The electronics module 80 includes a computer 82 including a processor 84 and a memory 86. The electronics module 80 is capable of executing software instructions implementing all or part of its functionality.

In one arrangement, a computer program product 88 including a computer readable medium (e.g. one or more CDROMs, diskettes, tapes, etc.) provides software instructions for all or part of the functionality of the electronics module 80, which can be installed on the computer 82 in the electronics module 80. Thus, the electronics module 80 is a combination of the computer 82 with installed software instructions.

The computer program product 88 can be installed by any suitable software installation procedure as is well known in the art. For example, in one arrangement, the computer program product is a CDROM, and an external CDROM drive is in electrical communication with the mobile phone 28 by a wire that plugs into a jack in the mobile phone 28. The user 24 can download a computer program or software application 87 including the software instructions for the electronics module 80 from the computer program product 88 on the CDROM to the computer 82 in the electronics module 80 using the jack in the mobile phone 28.

The software instructions can be downloaded over a wireless connection. A computer program propagated signal product 89 embodied on a propagated signal on a propagation medium (e.g. a radio wave, an infrared wave, a laser wave, sound wave, or an electrical wave propagated over the Internet or other network) provides software instructions for all or part of the functionality of the electronics module 80. The propagated signal is a signal that can be transmitted over the propagation medium over an extended period of time. In alternate arrangements, the propagated signal is an analog carrier wave or a digital signal carried on the propagated medium. For example, in one arrangement, the propagated signal is a digital signal propagated over the Internet or other network.

In another arrangement, the electronics module 80 is part of a mobile phone 28, and the computer application 87 including the software instructions is downloaded as a computer program propagated signal over the radio wave connection to the mobile phone 28 for installation on the computer 82 in the electronics module 32. If the mobile phone 28 has a wireless Internet connection, in one arrangement, the computer application 87 including the software instructions is downloaded as a computer program propagated signal from a Web site to the mobile phone 28 for installation in the computer 82 in the electronics module 32.

Figure 4:
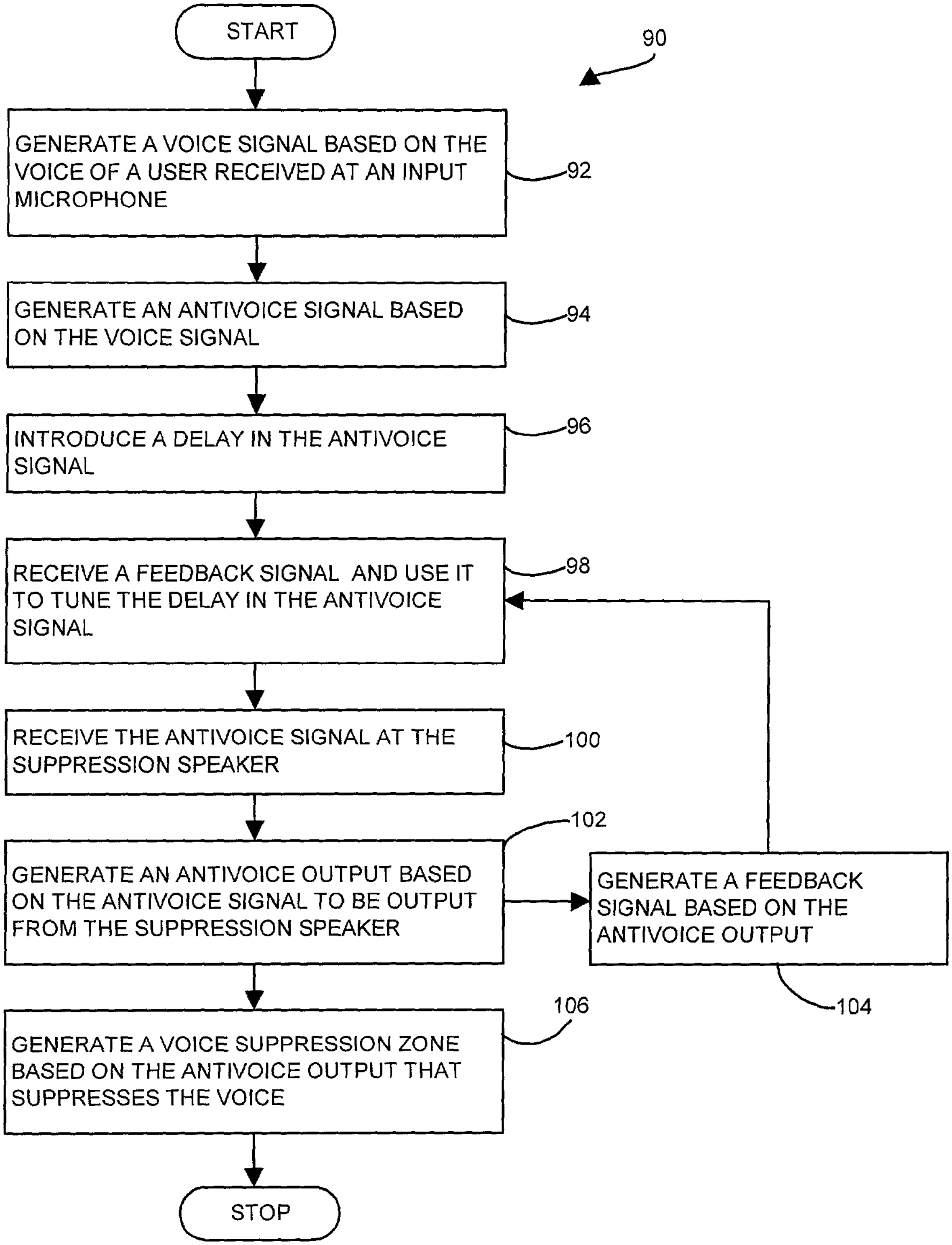
FIG. 4 shows a flow diagram of a procedure performed by the audio electronic device of FIG. 2 when in operation.

FIG. 4 provides a flow diagram explaining the procedure 90 performed by the audio electronic device 60 of FIG. 2 when in operation. In step 92, the input microphone receives a voice input 38 from a user 24 and generates a voice signal 62 based on the voice input 38. The electronics module 32 receives the voice signal 62 through the voice signal input 64 of the electronics module 32 and generates an antivoice signal 68 based on the voice signal 62 (step 94). In one arrangement, the antivoice signal 68 is opposite in phase to the voice signal 62. Then the electronics module 32 introduces a delay into the antivoice signal 68 (step 96). In one arrangement, the delay is based on the distance from the location of the input microphone 30 to the location of the suppression speaker 34. In step 96, the electronics module 32 receives a feedback signal 72-1 and uses the feedback signal 72-1 to tune the delay in the antivoice signal 68. In one arrangement, the electronics module 32 controls the length of the delay to insure that the antivoice output 42 based on the antivoice signal is opposite in phase to the voice 22 from the user 24. As described earlier, the feedback signal 72-1 is either a feedback signal 72-2 based on the antivoice signal, or a feedback signal 72-3 based on feedback input 76, which is in turn based on the antivoice output 42. In step 100, the suppression speaker 34 receives the antivoice signal 68 from the antivoice signal output 66 of the electronics module 32. Then, the suppression speaker 34 generates an antivoice output 42 based on the antivoice signal 68 (step 102). In one arrangement, the feedback microphone 74 converts the feedback input 76 into a feedback signal 72-3 (step 104), which the electronics module 32 receives as feedback signal 72-1 at the feedback input 70 of the electronics module 32 (see step 98). The antivoice output 42 forms a voice suppression zone 46 adjacent to the suppression speaker 34 (step 106). Within the voice suppression zone 46, the antivoice output 42 combines with the voice 22 to form a suppressed voice output 44 (see FIG. 1).

Another arrangement of the audio electronic device 60 is enabled selectively to suppress a selected voice, sound, or noise, such as to suppress certain distracting sounds or noises produced by the user 24, and serves as a voice correction device rather than as an audio privacy device. In this case, the user 24 is speaking with an intended listener, not an unintended listener 26, and the user 24 intends for his message to be heard without distraction. For example, a user 24 with a hacking cough, compulsive sneezing, or other intermittent distracting noise, uses an audio electronic device 60, which has been programmed to produce antivoice output 42 to suppress the intermittent distracting noise, but not to suppress a normal conversational voice. In this case, the audio electronic device 60 is programmed to recognize a certain voice pattern, such as cough, and enables the antivoice output 42 when that voice pattern occurs. In another arrangement, the audio electronic device 60 includes voice recognition software that learns the patterns of the voice 22 of a user 24, as is known in the art for voice and speech recognition software.

In various arrangements, the electronics module 32 of FIG. 2 is implemented as analog circuitry, digital circuitry, or a combination of analog and digital circuitry.

Figure 5:
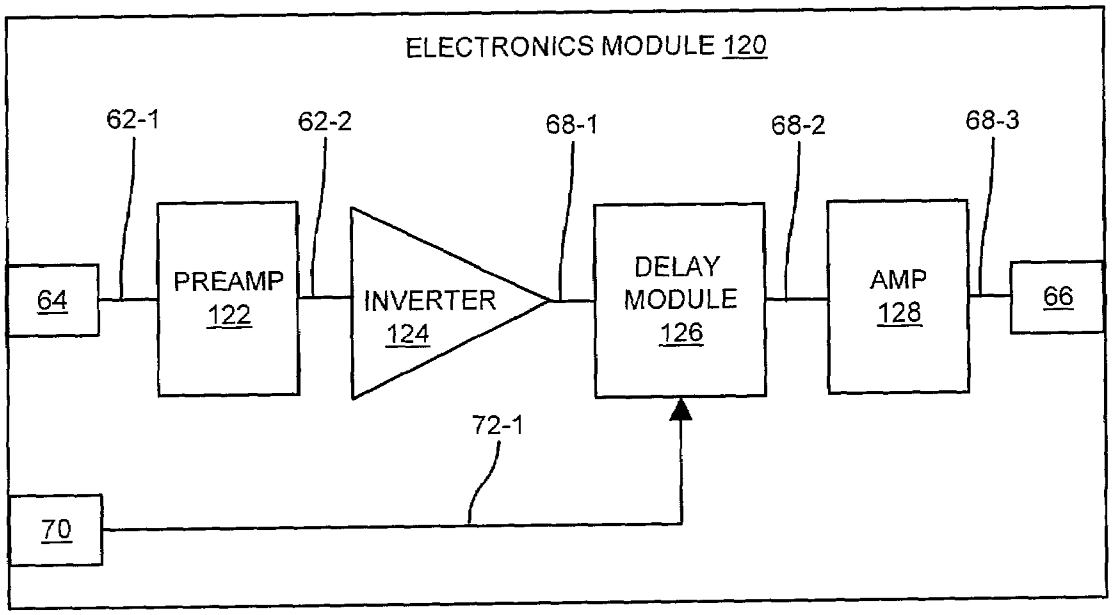
FIG. 5 shows, by way of example only, a block schematic diagram of an arrangement of an electronics module suitable for use in the audio electronics device of FIG. 2, including a preamplifier, an inverter, a delay module, and an amplifier.

FIG. 5 provides, by way of example only, additional detail for an electronics module 120 suitable for use with the invention as one instance of the electronics module 32 shown in FIG. 2. The electronics module 120 in FIG. 5 includes a preamplifier 122, an inverter 124, a delay module 126, an amplifier 128, the voice signal input 64, the feedback input 70, and the antivoice signal output 66.

Figure 6:
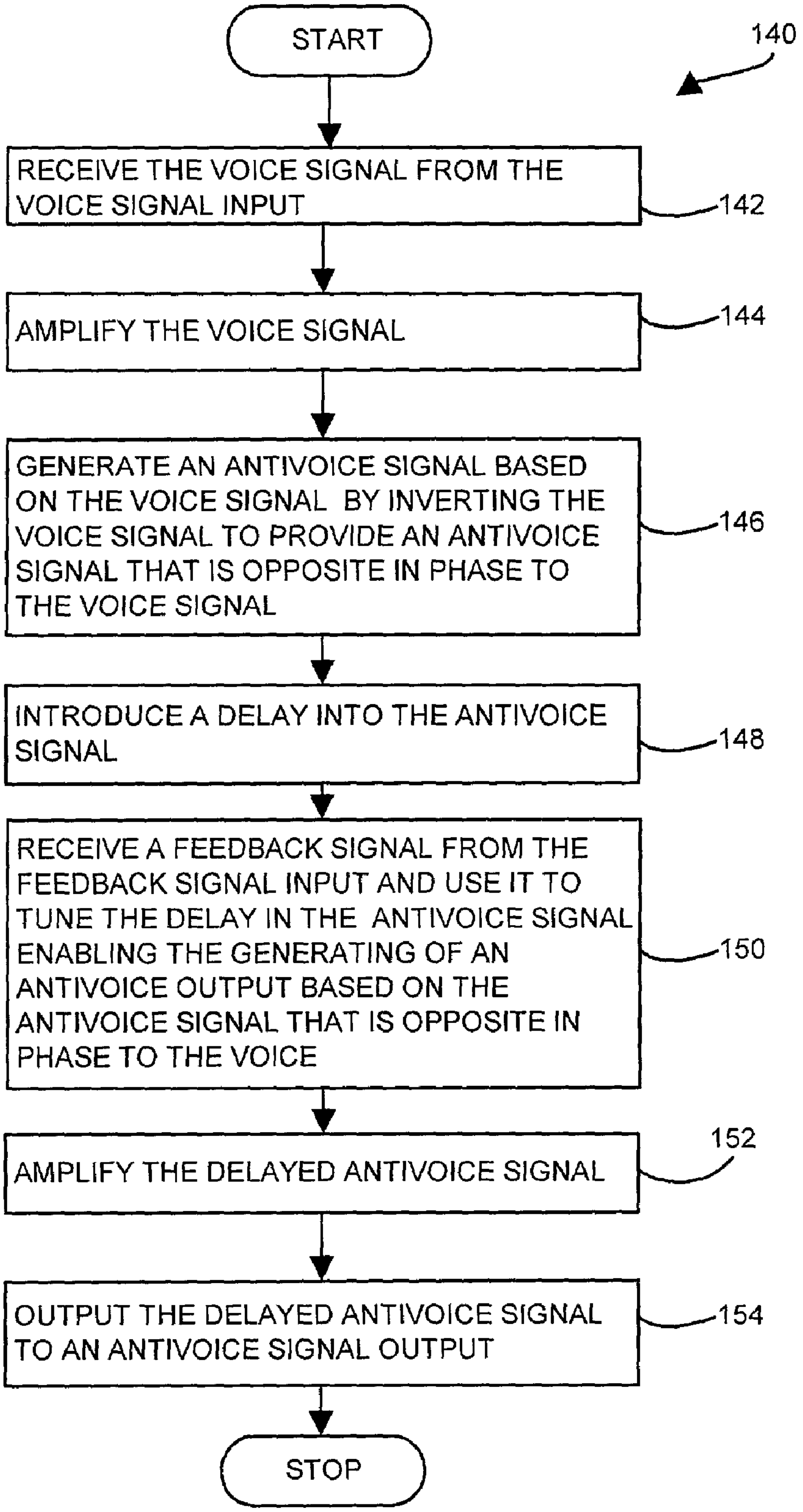
FIG. 6 shows a flow diagram of a procedure performed by the electronics module of FIG. 5 when in operation.

FIG. 6 provides a flow diagram explaining the procedure 140 performed by the electronics module 120 of FIG. 5. In step 142, the preamplifier 122 receives the voice signal 62-1 through the voice signal input 64 of the electronics module 120. The preamplifier 122 amplifies the voice signal 62-1 to produce the amplified voice signal 62-2 (step 144). The inverter 124 generates an antivoice signal 68-1 based on the amplified voice signal 62-2 by inverting the amplified voice signal 62-2 to provide an inverted signal or antivoice signal 68-1 which is opposite in phase to the amplified voice signal 62-2 (step 146). The delay module 126 introduces a delay into the antivoice signal 68-1 to produce a delayed antivoice signal 68-2 (step 148). The delay module 126 also receives a feedback signal 72-1 through the feedback input 70 of the electronics module 120. The delay module 126 uses the feedback signal 72-1 to tune the delay in the delayed antivoice signal 68-2 (step 150). The delay module 126 tunes the delay by using the feedback signal 72-1 to control a length of the delay in the delayed antivoice signal 68-2 by increasing or decreasing the length of the delay so that the antivoice output 42 generated later in the process by the suppression speaker 34 is opposite in phase to the voice 22. The delay module 126 also uses the feedback signal 72-1 to filter out any antivoice output 42 received at the input microphone 30.

In one arrangement, the delay is based on the distance from a location of the input microphone 30 and the location of the suppression speaker 34. This delay is introduced to account for the faster speed of electronic processing in the electronics module 120 than the speed of sound as the voice 22 travels through the air over the distance from the input microphone 30 to the suppression speaker 34. If the antivoice output 42 is provided without any delay, then the antivoice output 42 would not be out of phase with the voice 22 and would not effectively suppress the voice 22.

In step 152, the amplifier 128 then amplifies the delayed antivoice signal 68-2 to provide an amplified delayed antivoice signal 68-3 (step 152). The electronics module 120 outputs the amplified delayed antivoice signal 68-3 through the antivoice signal output 66 to provide the basis for the antivoice output 42.

Figure 7:
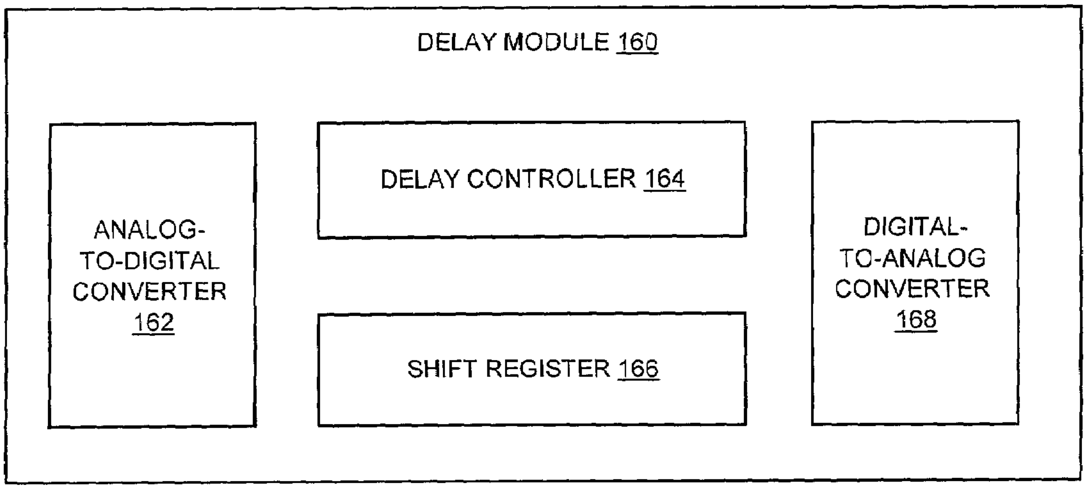
FIG. 7 shows, by way of example only, a block diagram of an arrangement of a delay module suitable for use in the electronics module of FIG. 5 including an analog-to-digital converter, a delay controller, a shift register, and a digital-to-analog converter.

FIG. 7 shows, by way of example only, a block diagram providing additional detail for a delay module 160 suitable for use with the invention as one instance of the delay module 120 shown in FIG. 5. The delay module 160 includes circuitry for an analog-to-digital converter 162, a delay controller 164, a shift register 166, and a digital-to-analog converter 168. The delay module 160 is implemented, in one arrangement, as an ASIC. The delay module 160 provide electrical connections that provide electrical communication among the analog-to-digital converter 162, the delay controller 164, the shift register 166, and the digital-to-analog converter 168. The analog-to-digital converter 162 and digital-to-analog converter 168 are based on converter circuitry as is well known in the electronics art. The shift register 166 is based on shift register circuitry as is well known in the art.

Figure 8:
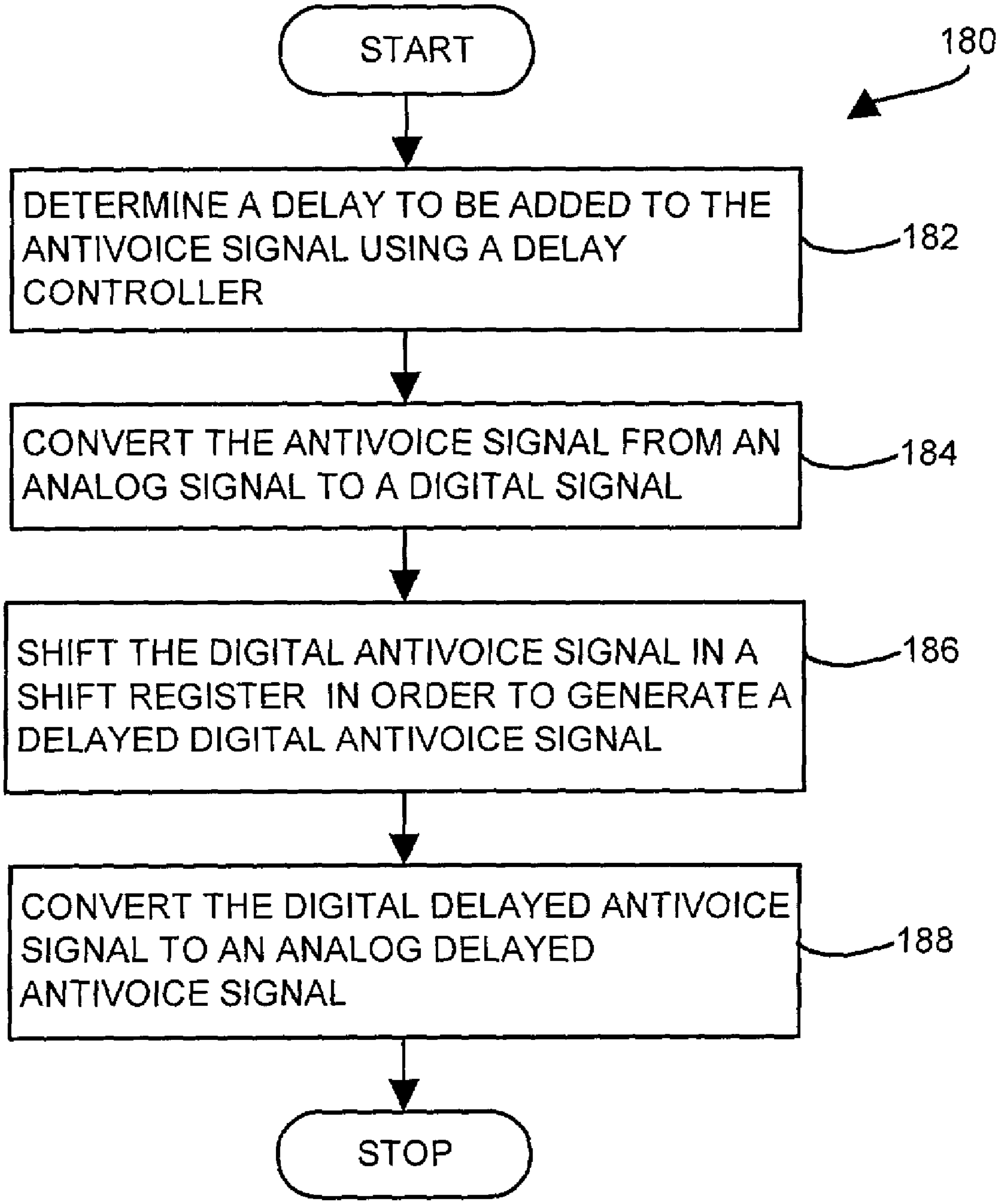
FIG. 8 shows a flow diagram of a procedure performed by the delay module of FIG. 7 when in operation.

FIG. 8 shows a flow diagram explaining the procedure 180 performed by the delay module 160 of FIG. 7 when in operation. In step 182, the delay controller 164 determines a delay to be added to the antivoice signal 68-1. The delay controller 164 determines this delay based on a distance from a location of the input microphone 30 and the suppression speaker 34, as described earlier for FIG. 6. The delay controller 164 then increases or decreases the amount of the delay an additional amount based on the feedback signal 72. The analog-to-digital converter 162 converts the antivoice signal 68-1 to a digital signal (step 184). The shift register 166 shifts the digital signal the amount of delay determined by the delay controller 164 (step 186). The digital-to-analog converter 168 converts the digital signal to an analog signal to provide a analog delayed antivoice signal 68-2 (step 188).

Figure 9:
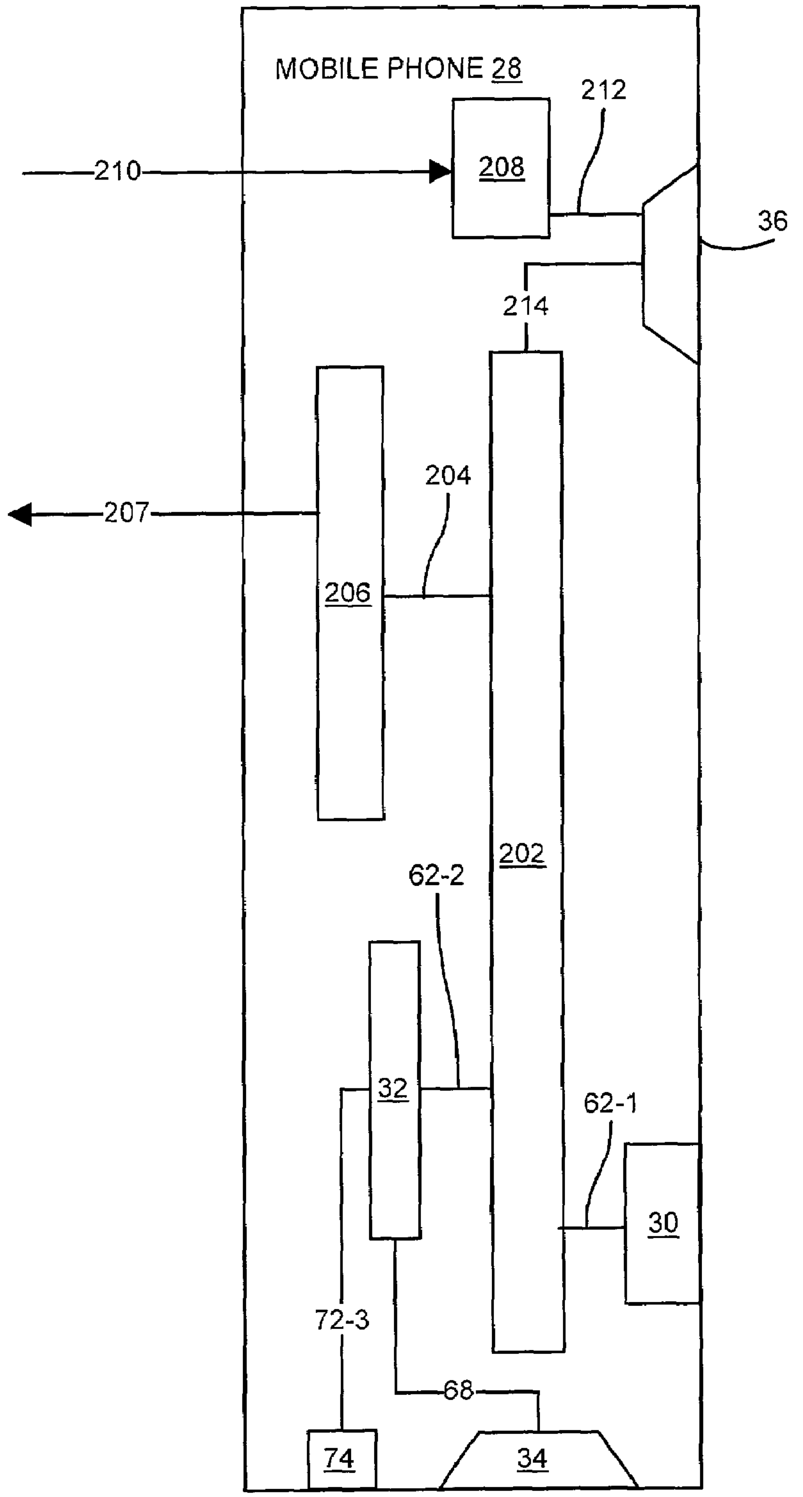
FIG. 9 shows, by way of example only, a view of an arrangement of a mobile phone device suitable for use in the audio privacy system shown in FIG. 1.

FIG. 9 shows, by way of example only, a view of a mobile phone device 28 suitable for use with the audio privacy system 20 of FIG. 1. The mobile phone device 28 includes an input microphone 30, an electronics module 32, a suppression speaker 34, a feedback microphone 74, a personal speaker 36, a phone controller 202, a transmitter 206, and a receiver 208. The input microphone 30 outputs an analog voice signal 62-1 to the phone controller 202. The phone controller 202 is a controller typical of the electronic circuitry used in a mobile phone, such as a cellular phone or satellite phone, that processes an incoming voice signal 62 when preparing a transmit signal 204 to be transmitted by a transmitter 206

In alternate arrangements, the electronics module 32 is incorporated into or combined with the phone controller 202. For example, in one arrangement, the electronics module 32 and phone controller 202 are combined onto one integrated circuit.

The transmitter 206 is a transmitter as it typically used in mobile phones, as is well known in the art, to send an outgoing signal 207 to another mobile phone usually by a wireless radio approach. The receiver 208 is a receiver as is typically used in mobile phones, as is well known in the art, to receive an incoming signal 210, process the incoming signal 210, and send an output signal 212 to the personal speaker 36 so that the user 24 hears the output signal 212 from the personal speaker 36. In one arrangement, the volume of the output signal 212 to the personal speaker 36 is increased slightly in comparison to conventional models to make up for a loss in fidelity of the voice 22 in the user's 24 other ear due to the antivoice output 42. The phone controller 202 also provides a duplicate signal 214 which is a duplicate of the voice signal 62-1. The phone controller 202 outputs the duplicate signal 214 to the personal speaker 36 so that the user 24 hears a representation of his or her own voice in the personal speaker 36 while he or she is talking into the input microphone 30.

In one arrangement, the phone controller 202 provides voice processing circuitry that produces a digitized voice signal 62-2 based on the voice signal 62-1. The electronics module 32 receives the digitized voice signal 62-2 and generates an antivoice signal 68 based on the digitized voice signal 62-2. The electronics module 32 outputs the antivoice signal 68 to the suppression speaker 34. In one arrangement of the invention, the electronics module 32 includes a digital-to-analog converter (see FIG. 7) that converts a digitized signal based on the digitized voice signal 62-2 to an analog antivoice signal 68 suitable for use by the suppression speaker 34. In another arrangement, the electronics module 32 also receives a feedback signal 72-3 from a feedback microphone 74. The electronics module 32 uses the feedback signal 72-3 to modify the antivoice signal 68.

Figure 10:
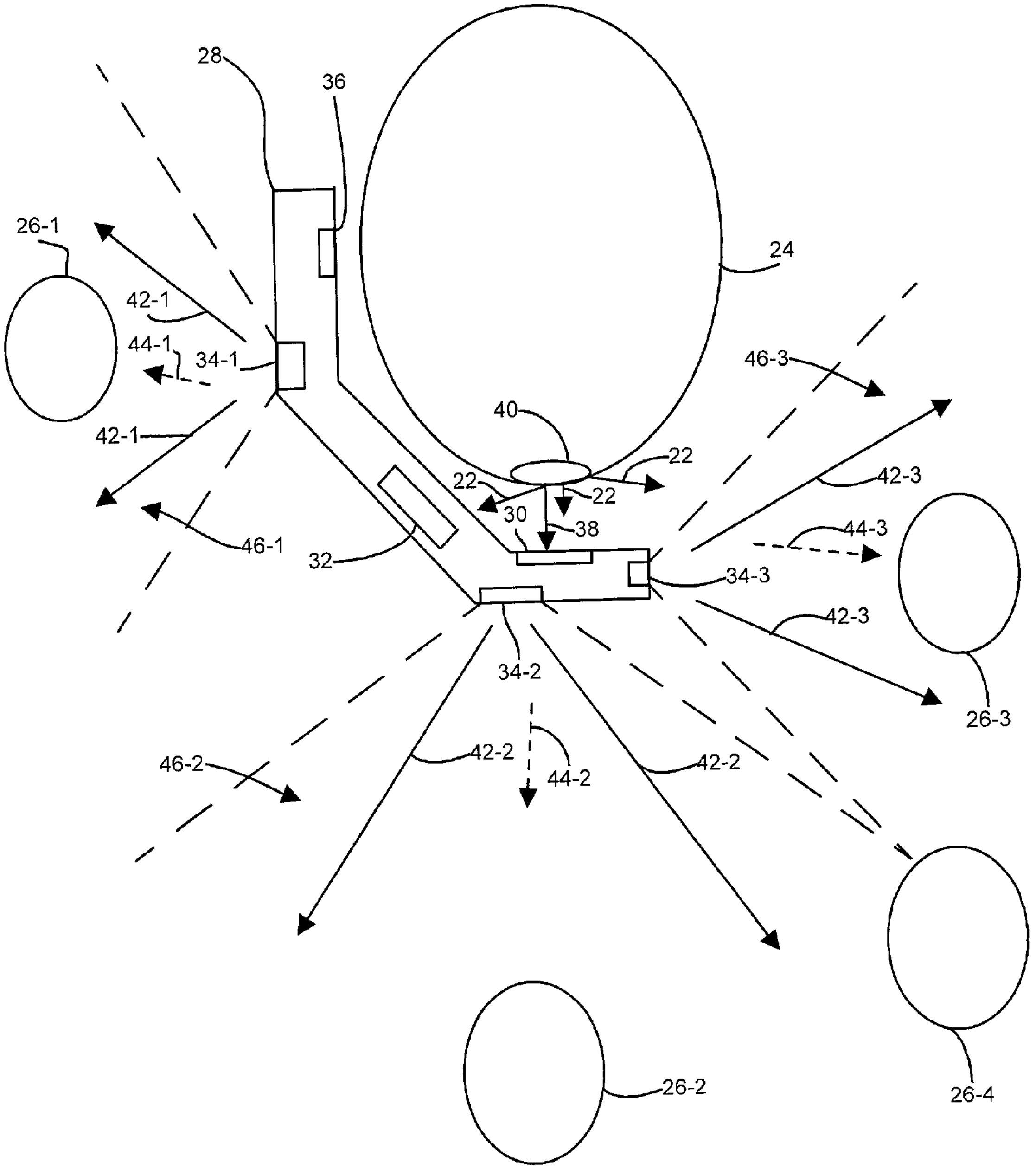
FIG. 10 shows, by way of example only, an overhead view of an arrangement of a mobile phone device including a plurality of voice suppression speakers generating a plurality of voice suppression zones.

FIG. 10 shows, by way of example only, an overhead view of a mobile phone device 28, including a plurality of voice suppression speakers, 34-1, 34-2, 34-3. The mobile phone device 28 includes an input microphone 30 for receiving the voice input 38 from the user 24, an electronics module 32, and a plurality of voice suppression speakers, 34-1, 34-2, 34-3 generating a plurality of antivoice outputs

42-1, 42-2, 42-3 forming a plurality of voice suppression zones 46-1, 46-2, 46-3. The antivoice outputs 42-1, 42-2, 42-3 combine with the voice 22 to form the suppressed voice outputs 44-1, 44-2, 44-3. The unintended listener 26-2 cannot understand or has difficulty understanding the suppressed voice output 44-2 in the voice suppression zone 46-2 that encompasses the unintended listener 26-2. The other voice suppression zones 46-1 and 46-3 may encompass other unintended listeners 26-1 and 26-3. In addition, if the unintended listener 26 moves out of the voice suppression zone 46-2, he or she is likely to encounter another one of the multiple voice suppression zones 46-1, 46-2, 46-3. For example, voice suppression zone 46-1 encompasses unintended listener 26-1 and voice suppression zone 46-3 encompasses unintended listener 26-3. Also, at a sufficient distance, or if two or more of the suppression speakers 34-1, 34-2, 34-3 are located near each other, then a merged voice suppression zone 46-4 is produced such as the merger of voice suppression zones 46-2 and 46-3 for unintended listener 26-4.

The invention is not limited to three suppression speakers 34-1, 34-2, 34-3 located at the front or the sides of the user 24 of the mobile phone 28, as shown in FIG. 10. In another arrangement, the mobile phone 28 includes a different number of suppression speakers. 34, which are placed on any available position on the mobile phone 28 not facing toward the user 24. Thus, in alternate arrangements, the suppression speakers 34 can be placed in other locations, such as directed rearward, or in several locations, to provide a circle of 360 degree coverage around the user 24 for the voice suppression zones 46. In another arrangement, the suppression speakers 34 are in electrical communication with the mobile phone 28 using a radio or other link to one or more suppression speakers 34, are located at a distance, such as several feet, from the mobile phone 28.

In a further arrangement of the invention, the suppression speakers 34-1, 34-2, 34-3 are capable of being selectively enabled or disabled and one or more of the suppression speakers 34-1, 34-2, 34-3 may be selected to provide the antivoice output 42-1, 42-2, 42-3. In one arrangement, the user 24 sees an unintended listener 26-2 in front of her and selects the voice suppression speaker 34-2 to be enabled. Typically, the user 24 makes the selection of the voice suppression speaker 34-2 through a switch, button, or voice command that provides a selection signal to the electronics module directing the electronics module to enable the antivoice output 34-2 for only that suppression speaker 34-2, while the other speakers 34-1 and 34-3 remain silent. This selection approach provides a benefit in that power is conserved by not powering all of the suppression speakers 34-1, 34-2, 34-3, thus extending battery life.

Another arrangement of the mobile phone 28 includes one or more direction detectors that the electronics module 32 uses to detect the directions of one or more unintended listeners 26. The direction detector uses radar, sonar, infrared radiation detection, or some other method to determine the direction of each unintended listener 26, as is known in the respective arts. The electronics module 32 then selectively enables one or more of the suppression speakers 34-1, 34-2, 34-3 in order to encompass the detected unintended listener 26 in one of the voice suppression zones 46-1, 46-2, 46-3. If the direction detectors no longer detect an unintended listener 26 after he or she leaves a voice suppression zone 46-1, 46-2 or 46-3, then the electronics module 32 selectively disables whichever voice suppression zone 46-1, 46-2, 46-3 that the electronics module 32 had previously enabled.

In an alternate arrangement, the mobile phone 28 includes one or more direction detectors and a movable suppression speaker 34 capable of being oriented in different directions by signals sent to the suppression speaker 34 from the electronics module 32. For example, in one arrangement, the suppression speaker 34 includes an electric motor that pivots the suppression speaker 34 so that it faces in different directions in response to a command from the user 24 or the electronics module 32.

The above-described features of the invention are well suited for use with devices manufactured by Cisco Systems, Inc. of San Jose, Calif.

While this invention has been particularly shown and described with references to preferred embodiments thereof, it will be understood by those skilled in the art that various changes in form and details may be made therein without departing from the spirit and scope of the invention as defined by the appended claims.

For example, it should be understood that the audio electronic device 60 is not limited to a mobile phone 28, such as a cellular phone or satellite phone. It should be understood that audio electronic device 60 can be any electronic device receiving audio input, such as a hands-free headset, recording device, computer, or other devices. The audio electronic device 60 can be any type of phone device that includes a transmitter 206 that generates a outgoing signal 207 that is capable of being received by another audio electronics device 60, a receiver 208 that is capable of receiving an incoming signal 210 from the other audio electronics device 60, and a personal speaker 36. The transmitter 206 can be a radio-based transmitter, such as in a cellular phone, cordless phone, or a satellite phone, or a transmitter 206 in a desk telephone that sends the outgoing signal 207 over a phone wire connected to a public telephone system. The receiver 208 can be a radio-based receiver or the receiver 208 in a desk telephone. In addition, the transmitter 206 of one audio electronic device 60 and the receiver 208 of another audio electronic device can communicate by infrared radiation, laser radiation, or radiation based on other parts of the electromagnetic spectrum. The audio electronic device 60 can be a computer with an input microphone 30, such as a laptop computer that a user 24 speaks into to communicate with the computer using speech recognition software.

It should be understood that the boundaries 48 of the voice suppression zone 46 shown in FIG. 1 are shown by way of example only. The suppression speakers 34 can be of different types that can produce voice suppression zones 46 of different sizes with different boundaries 48 than those shown in FIG. 1, depending on the type of suppression speaker 34.

The invention is not limited to voice input 38 based on a user 24 speaking an intelligible message. It should be understood that the voice input 38 to be suppressed can include other sounds than intelligible speech. Also, the voice input 38 can include music sung or played by an instrument into the input microphone 30. For example, the voice input 38 can include a tape recording or music from a radio played into the input microphone 30.

The invention does not require the voice input 38 to be provided by a person. It should be understood that the voice input 38 can be any voice 22 or audio input into the input microphone 30. The voice input 38 can be noise or sound provided by another living thing, such as an animal. The voice input 38 can be an intelligible message, a sound, or a noise made into the input microphone 30 by another device, such as a computer or a robot having a speaker of its own producing a voice input 38 for the input microphone 30.

It should be understood that all or part of the electronics module 32 can also be implemented as software instructions or program that executes on a general-purpose processor, such as an Intel® Pentium® microprocessor. For example, in one arrangement, the audio electronic device 60 is part of a general-purpose computer and the electronics module 32 is implemented as a software program or application that can be installed on the general-purpose computer from a computer program product. For example, a laptop computer can have an audio electronics device 60 incorporated into the laptop, in which case the electronics module 32 is implemented as a software module executing on the laptop computer.

It should be understood that the functional blocks shown in FIGS. 2, 5, 7, and 9 are not definitive and not meant to be limiting in any way. For example, it should be understood that the delay module 160 of FIG. 6 can be implemented as one circuit or integrated circuit chip. Alternatively, one or more parts of the delay module 160, such as the analog-to-digital converter 162, the delay controller 164, the shift register 166, and the digital-to-analog converter 168, can be implemented as one or more circuits or one or more integrated chips. It should also be understood that various modifications can be made to the circuitry of the invention. For example, the circuitry for generating the delay can be placed before the circuitry for generating the antivoice signal 68. In other words, the voice signal 62 is first delayed, and then a delayed voice signal is inverted to generate the antivoice signal 68.

It should be understood that the invention is not limited to a single input microphone 30 or a single feedback microphone 74, as shown in FIG. 2. Rather, other arrangements of the invention can include multiple input microphones 30 used with a mobile phone 28 or other audio electronic device 60. In one arrangement, the invention includes multiple input microphones 30 at different positions on the mobile phone 28, each microphone 30 oriented to receive the voice 22 of the user 24. In a further arrangement, the mobile phone 28 includes multiple input microphones 30 used with multiple suppression speakers 34. Each suppression speaker 34 is associated with an input microphone 30. Typically, each suppression speaker 34 is associated with the input microphone 30 that is closest to it. The electronics module 32 determines the delay for each suppression speaker 34 separately and determines a separate antivoice signal 68 for each suppression speaker 34. The delay for the antivoice signal 68 for a particular suppression speaker 34 is based on the distance from that suppression speaker 34 to its associated input microphone 30.

In one arrangement, the invention includes multiple input microphones 30 to detect the orientation of the voice 22 relative to the position of the mobile phone 28. The invention then uses this information on the orientation of the voice 22 to more effectively output the antivoice output 42 into a voice suppression zone 46. For example, the orientation of one or more suppression speakers 34 may be changed in response to the orientation of the voice 22 to change the direction of the antivoice output 42.

In a further arrangement, the invention includes multiple feedback microphones 74. For example, a feedback microphone 74 is associated with each suppression speaker 34. The electronics module 32 uses the feedback signal 72 associated with a particular suppression speaker 34 in determining the delay in the antivoice signal 68 for that suppression speaker 34.

The invention claimed is:

1. An audio electronic device comprising an audio privacy feature for suppressing a voice, comprising:

an input microphone that generates a voice signal in response to a voice input;

an electronics module, in electrical communication with the input microphone, that receives the voice signal from the input microphone and generates an antivoice signal based on the voice signal, wherein the electronics module comprises an inverter that inverts the voice signal into the antivoice signal so that the antivoice signal is opposite in phase to the voice signal, and a delay module that introduces a delay in the antivoice signal so that the antivoice output generated from the delayed antivoice signal is opposite in phase to the voice input, and wherein the delay module controls a length of the delay based on a feedback signal;

a suppression speaker, in electrical communication with the electronics module, that receives the antivoice signal from the electronics module and generates an antivoice output from the antivoice signal, wherein the antivoice output combines with the voice to form a voice suppression zone adjacent to the suppression speaker; and a feedback microphone in electrical communication with the electronics module, wherein the feedback microphone converts the antivoice output into the feedback signal and wherein the electronics module receives the feedback signal from the feedback microphone.

2. The audio electronic device of claim 1, wherein the delay is based on a distance from the input microphone to the suppression speaker.

3. The audio electronic device of claim 2, wherein the feedback signal is based on the delayed antivoice signal.

4. The audio electronic device of claim 1, further comprising a transmitter that generates a transmit signal that is capable of being received by another audio electronics device, a receiver that is capable of receiving a remote signal from the other electronics device, and a personal speaker that provides a user output in response to the remote signal.

5. The audio electronic device of claim 4, wherein the audio electronic device is a phone device.

6. The audio electronic device of claim 5, wherein the phone device is a wireless, hand-held phone.

7. The audio electronic device of claim 1, wherein the audio electronic device is a computerized device.

8. An audio electronic device comprising an audio privacy feature for suppressing a voice, comprising:

an input microphone that generates a voice signal from the voice input received at the input microphone;

an electronics module in electrical communication with the input microphone that receives the voice signal from the input microphone and generates a plurality of antivoice signals based on the voice signal;

a plurality of suppression speakers having different orientations from each other that receive the plurality of antivoice signals from the electronics module and generate a plurality of antivoice outputs from the plurality of antivoice signals, wherein the plurality of antivoice signals combine with the voice to generate at least one voice suppression zone adjacent to the plurality of suppression speakers; and a feedback microphone in electrical communication with the electronics module, wherein the feedback microphone converts the antivoice output into the feedback signal and wherein the electronics module receives the feedback signal from the feedback microphone.

9. The audio electronics device of claim 8, wherein the electronics module comprises an inverter that inverts the voice signal to provide the plurality of antivoice signals so that the plurality of antivoice signals are opposite in phase to the voice signal, and a delay module that introduces a delay into each antivoice signal so that each antivoice output generated from each delayed antivoice signal is opposite in phase to the voice.

10. An electronics module for use in an audio privacy device suppressing a voice, comprising:

a voice signal input that receives a voice signal representative of the voice of a user input into an input microphone;

an antivoice signal output that provides an antivoice signal;

a controller that receives the voice signal from the voice signal input and generates the antivoice signal based on the voice signal so that the antivoice signal enables a suppression speaker to generate an antivoice output based on the antivoice signal that combines with the voice to form a voice suppression zone adjacent to the suppression speaker;

a delay module, wherein the controller inverts the voice signal into the antivoice signal so that the antivoice signal is opposite in phase to the voice signal and the delay module introduces a delay in the antivoice signal so that the antivoice output generated from the delayed antivoice signal is opposite in phase to the voice input; and a feedback signal input receiving a feedback signal representative of the delayed antivoice signal that tunes the delay.

11. The electronics module of claim 10, wherein the antivoice signal is a digital signal, and the electronics module further comprises:

a shift register that introduces the delay into the digital antivoice signal, and a digital-to-analog converter that generates an analog antivoice signal from the delayed digital voice signal.

12. The electronics module of claim 10 wherein the antivoice signal is an analog signal, and the electronics module further comprising an analog-to-digital converter that generates the digital antivoice signal from the analog antivoice signal.

13. A method for suppressing a voice received by an unintended listener to the voice, the steps comprising:

generating a voice signal based on a voice input of a user;

generating an antivoice signal based on the voice signal by (1) inverting the voice signal to provide the antivoice signal so that the antivoice signal is opposite in phase to the voice signal, and (2) adding a delay to the antivoice signal so that an antivoice output to be generated from the delayed antivoice signal is opposite in phase to the voice input of the user, a length of the delay being controlled based on a feedback signal;

generating the antivoice output based on the delayed antivoice signal, the antivoice output being combined with the voice in order to suppress the voice received by the unintended listener located in a voice suppression zone formed by the antivoice output; and generating the feedback signal in a feedback microphone by converting the antivoice output into the feedback signal.

14. The method of claim 13, further comprising the step of determining the delay based on a distance from an input location of the voice to an output location of the antivoice output.

15. The method of claim 13, further comprising the steps of orienting a direction of the antivoice output to direct the voice suppression zone to encompass a target location.

16. A computer readable medium having computer readable code thereon for suppressing a voice received by an unintended listener to the voice, the medium comprising:

instructions for receiving a voice signal based on the voice of a user;

instructions for generating an antivoice signal based on the voice signal by (1) inverting the voice signal to provide the antivoice signal so that the antivoice signal is opposite in phase to the voice signal, and (2) adding a delay to the antivoice signal so that an antivoice output to be generated from the delayed antivoice signal is opposite in phase to the voice input of the user, a length of the delay being controlled based on a feedback signal;

instructions for outputting the antivoice signal to a suppression speaker so that the antivoice signal enables the generating of an antivoice output based on the antivoice signal that combines with the voice in order to suppress the voice received by the unintended listener located in a voice suppression zone formed by the antivoice output;

wherein the feedback signal is generated by a feedback microphone converting the antivoice output into the feedback signal.

17. An audio electronic device comprising an audio privacy feature for suppressing a voice, comprising:

an input microphone that generates a voice signal in response to a voice input;

means for receiving the voice signal from the input microphone and generating an antivoice signal based on the voice signal;

a suppression speaker that receives the antivoice signal from the means for receiving and generating, and generates an antivoice output from the antivoice signal, wherein the antivoice output combines with the voice to form a voice suppression zone adjacent to the suppression speaker; and a feedback microphone in communication with said means for receiving and generating, wherein the feedback microphone converts the antivoice output into a feedback signal and provides said feedback signal to said means for receiving and generating.

18. An audio electronic device comprising an audio privacy feature for suppressing a voice, comprising:

an input microphone that generates a voice signal in response to a voice input;

an electronics module, in electrical communication with the input microphone, that receives the voice signal from the input microphone and generates an antivoice signal based on the voice signal, wherein the electronics module comprises an inverter that inverts the voice signal into the antivoice signal so that the antivoice signal is opposite in phase to the voice signal, and a delay module that introduces a delay in the antivoice signal so that the antivoice output generated from the delayed antivoice signal is opposite in phase to the voice input, and wherein the delay module controls a length of the delay based on a feedback signal;

a suppression speaker, in electrical communication with the electronics module, that receives the antivoice signal from the electronics module and generates an antivoice output from the antivoice signal, wherein the antivoice output combines with the voice to form a voice suppression zone adjacent to the suppression speaker and wherein the delay is based on a distance from the input microphone to the suppression speaker;

a feedback microphone located proximate said suppression speaker, said feedback microphone in electrical communication with the electronics module, wherein the feedback microphone converts the antivoice output into the feedback signal and wherein the electronics module receives the feedback signal from the feedback microphone, and wherein the audio electronic device is selected from the group comprising a phone device, a wireless hand-held phone and a computerized device; and a transmitter that generates a transmit signal that is capable of being received by another audio electronics device, a receiver that is capable of receiving a remote signal from the other electronics device, and a personal speaker that provides a user output in response to the remote signal.

* * * * *